United States Patent [19]

Niermann et al.

[11] Patent Number: 4,603,588
[45] Date of Patent: Aug. 5, 1986

[54] DEVICE FOR GRIPPING SPECIMENS

[75] Inventors: Hans Niermann, Essen; Klaus Köhnen, Mülheim/Ruhr; Joachim Jorde, Essen, all of Fed. Rep. of Germany

[73] Assignee: Krupp Koppers GmbH, Essen, Fed. Rep. of Germany

[21] Appl. No.: 633,097

[22] Filed: Jul. 20, 1984

[30] Foreign Application Priority Data

Dec. 22, 1983 [DE] Fed. Rep. of Germany ....... 3346429

[51] Int. Cl.⁴ .............................................. G01N 3/00
[52] U.S. Cl. ................................................... 73/794
[58] Field of Search ............... 73/761, 787–789, 73/826, 831–833, 847, 856, 857, 794, 795

[56] References Cited

U.S. PATENT DOCUMENTS

| | | | |
|---|---|---|---|
| 233,712 | 10/1880 | Thurston | 73/847 |
| 1,888,755 | 11/1932 | Barr et al. | 73/826 |
| 2,884,986 | 5/1959 | Heldenbrand | 73/831 |
| 3,610,031 | 10/1971 | Clark et al. | 73/789 |
| 4,196,635 | 4/1980 | Zuber et al. | 73/794 |

*Primary Examiner*—Stewart J. Levy
*Assistant Examiner*—Robert R. Raevis
*Attorney, Agent, or Firm*—Michael J. Striker

[57] ABSTRACT

A device for gripping a specimen for applying to the same tensile or torsional strain includes two plates spaced from each other and a tubular spacer extended between the two plates and accommodating a specimen. The specimen is attached to the plates by respective nuts. One end of the specimen extended outwardly from the respective plate and nut is formed by a threaded pin, on which a pulling device for applying tensile stress onto the specimen, is set. The other end of the specimen has a square portion to which a tap wrench is applied, which, with the aid of two bolts positioned on one of the plates, applies torsional strains to the specimen.

4 Claims, 2 Drawing Figures 4,603,588

DEVICE FOR GRIPPING SPECIMENS

BACKGROUND OF THE INVENTION

The present invention relates to a device for gripping specimens for applying thereon uniaxial or biaxial condition of stress.

It has been required at the present time to test the behavior of materials, particularly concerning their rigidity and resistance to corrosion in operational conditions under which they are in use. These conditions include gaseous or fluid media surrounding the materials as well as temperatures which are applied to the materials in a further process.

Clamping devices for gripping specimens have been utilized up till now, which have been used for testing materials in research or laboratory installations and were unsuitable for use in experimental or large installations.

SUMMARY OF THE INVENTION

It is an object of the present invention to provide a improved device for gripping specimens.

It is a further object of the present invention to provide a gripping device, which would determine behavior of a material under actually existing operational conditions.

These and other objects of the invention are defined by a device for gripping specimens for applying thereto uniaxial or biaxial condition of stress, comprising two plates spaced from each other; a spacer extended between said plates and respectively connected to said plates, said spacer accommodating a specimen, said specimen having two end portions extended outwardly from said spacer and projecting through and beyond the respective plates, said end portions each having a thread; two nuts screwed on said end portions so that they are brought into attachment with said plates, respectively, one of said end portions having a threaded pin extended outwardly from the respective nut, another of said end portions having a square end extended outwardly from the respective nut; a pulling device applied on said threaded pin to apply to the specimen a predetermined tensile stress; a wrench mounted on said square end; and two bolts positioned on one of said plates and acting on said wrench to apply a predetermined torsional strain to said specimen, said specimen extending through said one of said plates with a play, another of said plates having a square opening, said one end portion having a square portion which is received in said square opening.

The spacer may be formed by a tube.

The device may further include at least one wire strain gauge attached to the specimen, said spacer being formed with at least one lateral opening, said opening being sufficiently large to permit measurements on said wire strain gauge.

These openings provide a direct contact of the specimen positioned in the tube with surrounding gaseous and fluid media.

The whole device with a specimen gripped therein may be insertable into a laboratory or plant installation when the plant is in operation.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawing.

DETAILED DESCRIPTION OF THE PREFERRED EMBODIMENT

Figure 1:
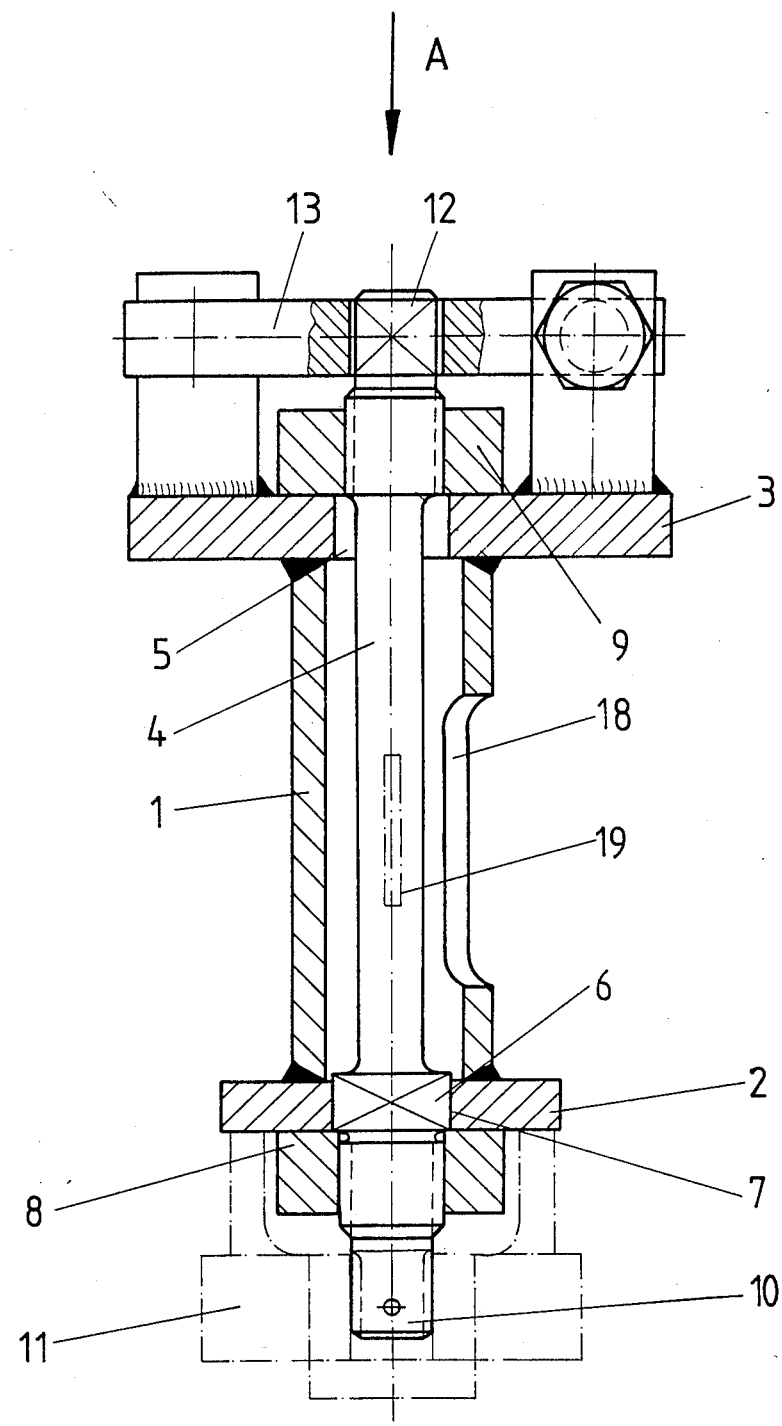
FIG. 1 is an axial sectional view through the device according to the invention.
Figure 2:
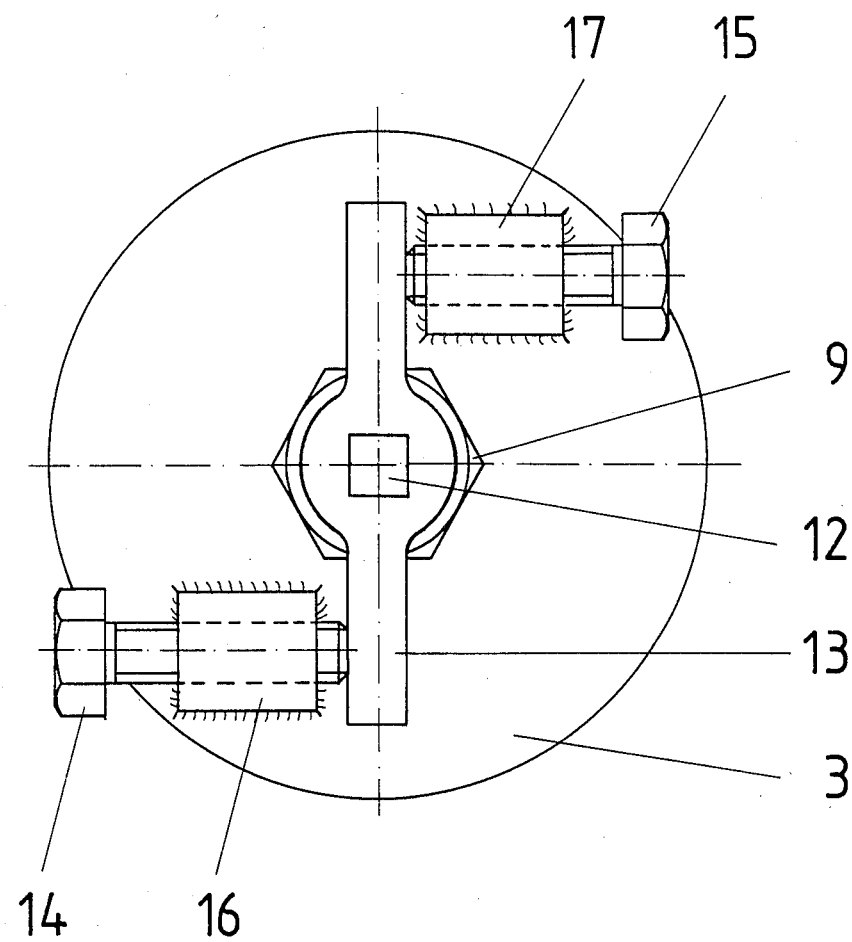
FIG. 2 is a plan view seen from arrow A of FIG. 1.

Referring now to FIGS. 1 and 2 in detail, the device for gripping a specimen for defining a state of stress therein includes a spacer 1 which is formed as a tube in the exemplified embodiment. A specimen 4 is inserted in tube 1 and extends outwardly from the ends thereof to penetrate two spaced plates 2 and 3. An opening 5 of the diameter greater than that of specimen 4 is formed in the upper plate 3 to receive the end portion of the specimen with a play. A square portion 6 is formed at the lower end of the specimen 4, which portion is engaged in a respective square opening 7 formed in the lower plate 2 so that the specimen is secured in plate 2 against rotation. Both ends of the specimen have threads on which respective nuts 8 and 9 are screwed, which thereby enclose the outer surfaces of plates 2 and 3.

The lower end of the specimen 4 extended downwardly beyond plate 2 and nut 8 is formed as a threaded pin 10, on which a device 11, preferably hydraulically operated, is applied.

The upper end of specimen 4 has a square portion 12 on which a tap wrench 13 is mounted. Two bolts 14 and 15, which are positioned in respective bearing supports or lugs 16 and 17, secured to plate 3, are applied to the tap wrench 13.

Tube 1 is provided with a lateral opening 18 through which the above mentioned gaseous or fluid medium can flow into the interior of tube 1 to flow in direct contact with the specimen. Opening 18 is sufficiently large to permit carrying out measurements on the specimen by means of a wire strain gauge 19 attached to the specimen in the known fashion. A number of openings or recesses 18 can be provided in tube 1 for a plurality of wire strain gauges, respectively.

Tensile stress or torsional strain or both can be precisely applied to a specimen gripped by the above-described device.

The applying of the tensile stress to the specimen 4 is carried out by the pulling device 11 with is applied to the threaded pin 10 of specimen 4, and with the aid of which the specimen is stretched to a required size.

Nut 8 is turned towards plate 2 according to the elongation of the specimen. Tensile stress of the specimen 4 is accurately defined and measured by wire strain gauge 19 due to the exactly measurable elongation of the specimen.

For applying torsional strain to the specimen 4, bolts 14 and 15 are first rotated by hand unless the resistance to rotation makes a further rotation of bolts 14, 15 impossible. Now an angular position or so-called zero position of tap wrench 13 is defined. By further rotating bolts 14 and 15 with a monkey wrench and by rotating the tap wrench 13 will the specimen 4 be tensioned at a required angle of rotation $\alpha$. The torsional strain in the specimen 4 will be calculated by comparison with the known rotation angle $\alpha$ and in accordance with known material constants for a given geometry of the specimen or determined by wire strain gauges.

In order to apply tensile stress or torsional stress to the specimen the above described steps can be combined.

The specimen can be formed as a rod or have any other various cross-sections; it can be also formed as a sheet strip. It is to be understood that the component parts of the gripping device would be then adjusted to a particular shape of the specimen.

The gripping device according to the invention has the following advantages:

(a) Due to comparatively small dimensions of the clamping or gripping device there is a possibility that it can be inserted with the specimen gripped, into the components of the operating research or industrial plants or laboratory installations, and values of stresses would be defined by behavior of the specimen in operational conditions;

(b) The device according to the invention offers a possibility to apply measurable deformations to the specimen to thereby precisely define a one dimensional or two-dimensional state of stress in the specimen;

(c) Stresses in the specimen do not change or change insignificantly, depending on ambient temperatures or temperature fluctuations under operational conditions. The coefficients of thermal expansion of the material being tested should substantially coincide with those of the materials of the components of the clamping device.

It will be understood that each of the elements described above, or two or more together, may also find a useful application in other types of clamping devices for clamping specimens for applying on the specimens uniaxial or biaxial condition of stress differing from the types described above.

While the invention has been illustrated and described as embodied in a gripping device for gripping specimens, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A device for gripping specimens for applying thereto uniaxial or biaxial condition of stress, comprising an upper plate and a lower plate spaced from each other; a spacer extended between said upper and lower plates and respectively connected to said plates, said spacer accommodating a specimen, said specimen having two opposite end portions extended outwardly from said spacer and projecting through and beyond the respective plate, said end portions each having a thread; two nuts screwed on said end portions so that they are brought into attachment with said plates, respectively, one of said end portions having a threaded pin extended outwardly from the respective nut, another of said end portions having a square end extended outwardly from the respective nut; a pulling device attached to said threaded pin to apply to the specimen a predetermined tensile stress; a wrench mounted on said square end; and two bolts positioned on said upper plate and acting on said wrench to apply a predetermined tensional strain to said specimen, said specimen extending through said upper plate with a play, said lower plate having a square opening, said one of said end portions having a square portion which is received in said square opening, said pulling device being supported immediately against said lower plate by pulling one of the end portions having said threaded pin relative to said lower plate;

said device with a specimen gripped therein being insertable into a laboratory or plant installation under corrosive operational conditions so as to test materials under corrosive operational conditions.

2. The device as defined in claim 1, wherein said spacer is a tube.

3. The device as defined in claim 2, wherein said tube is provided with at least one lateral opening.

4. The device as defined in claim 1, further including at least one wire strain gauge attached to the specimen, said spacer being formed with at least one lateral opening, said opening being sufficiently large to permit measurements on said wire strain gauge.

* * * * *